United States Patent
Potthast et al.

[19]

[11] Patent Number: 5,942,676
[45] Date of Patent: Aug. 24, 1999

[54] SENSOR FOR THE DETECTION OF COMBUSTIBLE GASES

[75] Inventors: Heidrun Potthast, Korntal-Muenchingen; Bernd Schumann, Rutesheim, both of Germany

[73] Assignee: Robert Bosch GmbH, Stuttgart, Germany

[21] Appl. No.: 08/860,549

[22] PCT Filed: Nov. 23, 1995

[86] PCT No.: PCT/DE95/01641

§ 371 Date: Jun. 20, 1997

§ 102(e) Date: Jun. 20, 1997

[87] PCT Pub. No.: WO96/19725

PCT Pub. Date: Jun. 27, 1996

[30] Foreign Application Priority Data

Dec. 20, 1994 [DE] Germany .................. 44 45 359

[51] Int. Cl.⁶ .................. G01N 27/04; G01N 27/12; B32B 9/00
[52] U.S. Cl. .................. 73/31.06; 73/23.31; 422/90; 422/94
[58] Field of Search .................. 73/31.06, 23.31; 422/90, 98, 94

[56] References Cited

U.S. PATENT DOCUMENTS

| | | |
|---|---|---|
| 4,792,433 | 12/1988 | Katsura et al. .................. 422/98 |
| 5,140,393 | 8/1992 | Hijikihigawa et al. .................. 357/25 |
| 5,147,523 | 9/1992 | Yagawara et al. .................. 204/424 |
| 5,330,855 | 7/1994 | Semancik et al. .................. 428/701 |
| 5,334,350 | 8/1994 | Friese et al. .................. 422/98 |
| 5,338,430 | 8/1994 | Parsonage et al. .................. 204/412 |
| 5,342,701 | 8/1994 | Miremadi et al. .................. 428/701 |
| 5,387,462 | 2/1995 | Debe .................. 428/245 |
| 5,618,496 | 4/1997 | Hatsumi et al. .................. 422/90 |
| 5,726,347 | 3/1998 | De Haan .................. 73/31.06 |
| 5,767,388 | 6/1998 | Fleishcer et al. .................. 73/31.06 |

FOREIGN PATENT DOCUMENTS

| | | |
|---|---|---|
| 0313390 | 10/1987 | European Pat. Off. . |
| 3624217 | 1/1987 | Germany . |

*Primary Examiner*—Richard Chilcot
*Assistant Examiner*—J. David Wiggins
*Attorney, Agent, or Firm*—Venable; George H. Spencer; Norman N. Kunitz

[57] ABSTRACT

A sensor for detecting combustible gases in a test gas. The core of this sensor is comprised of a sensitive layer based on a semiconducting metal oxide that is deposited on a ceramic substrate and for which the electrical resistance provides information on the concentration of combustible gases in a test gas. The sensitive layer (3) is comprised of a compound (12) of sintered-together grains (15) of the semiconducting metal oxide, the surface of which is coated with gold and/or a gold alloy. The semiconducting metal oxide in this case is stannic oxide ($SnO_2$), indium oxide ($In_2O_3$), titanium oxide ($TiO_2$) or another n-semiconducting metal oxide or metal mix oxide. The gold alloy, for example, is composed of 66 mol % gold and 33 mol % palladium (Pd).

23 Claims, 2 Drawing Sheets

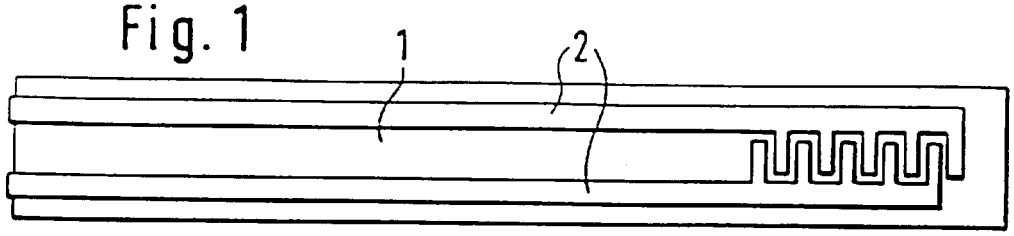
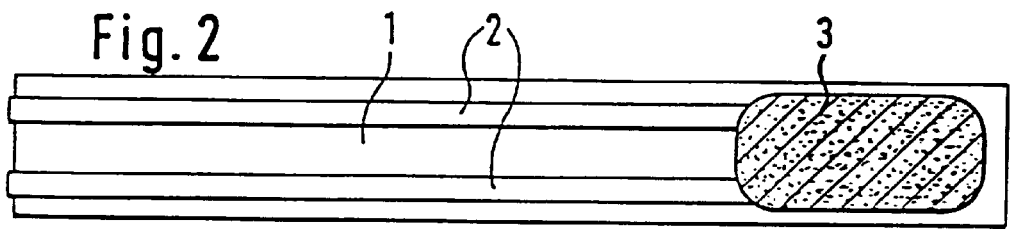
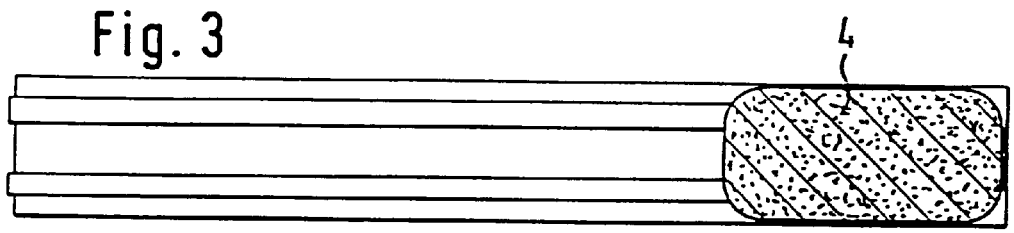
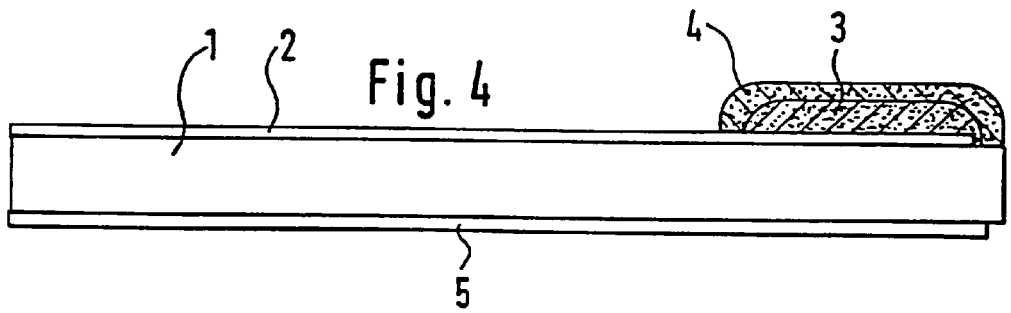
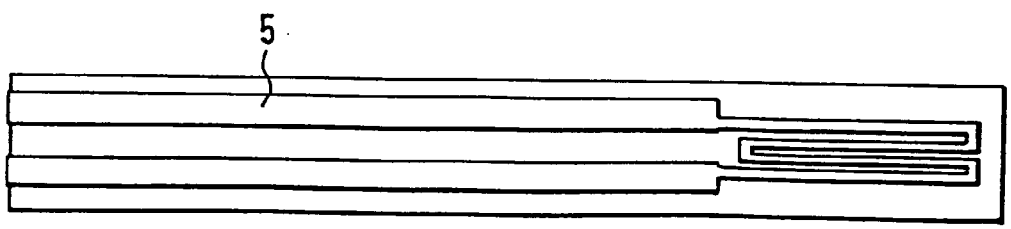

SENSOR FOR THE DETECTION OF COMBUSTIBLE GASES

PRIOR ART

The invention concerns a sensor for the detection of combustible gases in a test gas, having a sensitive layer on the basis of a semiconducting metal oxide that is deposited on an insulating, ceramic substrate, and for which the electrical resistance provides a statement of the concentration of combustible gases in a test gas. The invention further relates to a process for the manufacture of a sensitive layer of type for gas sensors, which determine the combustible gas component in a test gas by evaluating the electrical resistance of the sensitive layer. The use of sensors for detecting specific components of a test gas is known, which sensors have a sensitive element composed of a semiconductor material, the electrical resistance of which changes when coming in contact with the specific gas component. Sensors of this type are used, in particular, for determining the oxygen content in exhaust gases, e.g. from piston-type internal combustion engines, but also for determining methane, carbon-monoxide or alcohol. The semiconductor materials used are in particular semiconducting metal oxides such as stannic oxide ($SnO_2$), zinc oxide (ZnO), titanium oxide ($TiO_2$) or tungsten oxide ($WO_3$), depending on the purpose. These known sensors normally are produced with the thick or thin-layer technique. Conductor tracks, by means of which the change in resistance is determined later on, are applied onto an insulating, preferably a ceramic substrate, e.g. made of aluminum oxide ($Al_2O_3$), as well as the semiconducting metal oxide. In order to increase on the one hand the sensor sensitivity—which depends on the temperature—and to ensure on the other hand that the thermodynamic balance of absorption and desorption is maintained, it is standard practice to heat the substrate with the sensor arrangement. In accordance with known suggestions, the heating devices needed for this are arranged, for example, on the underside of the substrate—wherein the sensor arrangement is located on the top—or they can be integrated into the substrate or arranged between substrate surface and sensor arrangement. A sensor of this type is known, for example, from the EP-OS 313 390. The sensor following from this reference has a substrate composed of aluminum oxide ($Al_2O_3$) with a heating device as well as a sensor arrangement placed onto one side. As semiconducting material, stannic oxide ($SnO_2$) is suggested for detecting methane, tungsten oxide ($WO_3$) for detecting carbon monoxide or lanthanum nickel oxide ($LaNiO_3$) for detecting alcohol.

A similar sensor, for which the heating device is integrated into a substrate composed of aluminum oxide ($Al_2O_3$), is known from the DE-OS 36 24 217. The gas-sensitive semiconductor layer for this sensor is composed of a porous titanium dioxide ($TiO_2$) enriched with a second metal oxide. The described sensor is provided in particular for regulating the air/fuel ratio in an exhaust gas by measuring the oxygen content.

These known sensors on a semiconductor basis have proven themselves in practical operations for detecting combustible gases, such as carbon monoxide (CO), hydrogen ($H_2$) and hydrocarbons. However, all known sensors have a tendency to a transverse sensitivity relative to nitric oxides, such as occur, for example, in the gaseous atmosphere during combustion processes or in automotive exhaust gases. If used in nitric-oxide containing test gases, the known sensors therefore provide inaccurate results or require special correction devices.

It is the object of the invention to provide a sensor as well as a process for manufacturing a sensitive layer, which permits a sufficiently good detection of the share of combustible gases even in test gases with a nitric-oxide component.

The above object is generally achieved according to a first aspect of the invention by a sensor for detecting combustible gases in a test gas, including a sensitive layer on the basis of a semiconducting metal oxide that is deposited on an insulating, ceramic substrate, and for which the electrical resistance delivers a statement on the concentration of combustible gases in a test gas, wherein the sensitive layer has a structural composition of sintered together grains of the semiconducting metal oxide and the surface of this composition is coated with gold and/or a gold alloy.

The above object is generally achieved according to a further aspect of the invention by a process for manufacturing a sensitive layer for gas sensors, which determine the combustible gas component in a test gas by evaluating the electrical resistance of the sensitive layer, including the following steps:

producing a powder on the basis of a semiconducting metal oxide with components of an oxide that increases the conductivity, of palladium, as well as of a 2- or 3-valent element of the alkaline earth or the rare earths;

coating the powder grains with gold and/or an alloy of gold and one or several precious metals of the group palladium (Pd), platinum (Pt), rhodium (Rh), iridium (Ir), osmium (Os);

producing a paste from the coated powder grains;

applying the paste to a sensor substrate as the sensitive layer; and sintering the sensitive layer on the substrate at 500° to 1000° C., preferably 700° C.

The inventive features of the sensor defined by independent claims 1 to 10 can be produced with techniques that are known on principle and thus can be produced cost-effectively. It reacts swiftly and with good sensitivity to combustible gases contained in a test gas, without being simultaneously affected by nitric-oxide components in the test gas. It is therefore particularly well suited for use in motor vehicles, e.g. to control the ventilation of the inside area, which it may interrupt if exhaust gases reach the inside as well as for measuring small concentrations of combustible gases in the air or in exhaust gases from firings of combustion engines.

Advantageous modifications and useful embodiments of the inventive sensor respectively the process for manufacturing it follow from the dependent claims.

The sensitivity and speed of the sensor with respect to the predetermined use can be adjusted by doping the semiconducting oxide used for the sensitive layer with palladium (Pd).

The excellent function of the suggested sensor is due to the inventive coating of the sensitive semiconductor oxide with gold or a gold alloy. It prevents the absorption of the nitric-oxides occurring in the test gas. As a result of this, the sensor can detect low concentrations of combustible gases, such as are standard for road traffic, with a stable basic resistance, without experiencing a permanent increase in the resistance or a drift if nitric-oxide containing gases impinge on the sensor.

The suggested sensor furthermore is well suited for a summary determination of the content of combustible gases in the exhaust gas from furnaces in dependence on its oxygen content.

It is advantageous if an oxide that increases conductivity, e.g., tantalum oxide, is added to the metal oxide, which is used as base material for the sensitive layer. Another, advantageous improvement of the sensor effect is achieved by doping the base material with a material that acts as a diffusion blocking agent, especially palladium. It is also advantageous if a bivalent or trivalent element of the alkaline earths or the rare earths is added to the basic material for the sensitive layer, for example, magnesium oxide, to prevent the metal oxide that is present in the form of grains from sintering together too strongly.

It is preferable if the semiconducting metal oxide used is stannic oxide.

The suggested sensor as well as the process for manufacturing a sensitive layer are explained in the following in more detail and with the aid of the embodiments shown in the drawing.

BRIEF DESCRIPTION OF THE DRAWINGS

FIGS. 1 to 3 show stages in the production of a sensor as seen from above. FIG. 4 shows a view from the side of the sensor. FIG. 5 shows the sensor in a view from below.

DETAILED DESCRIPTION OF THE PREFERRED EMBODIMENTS

Figure 6:
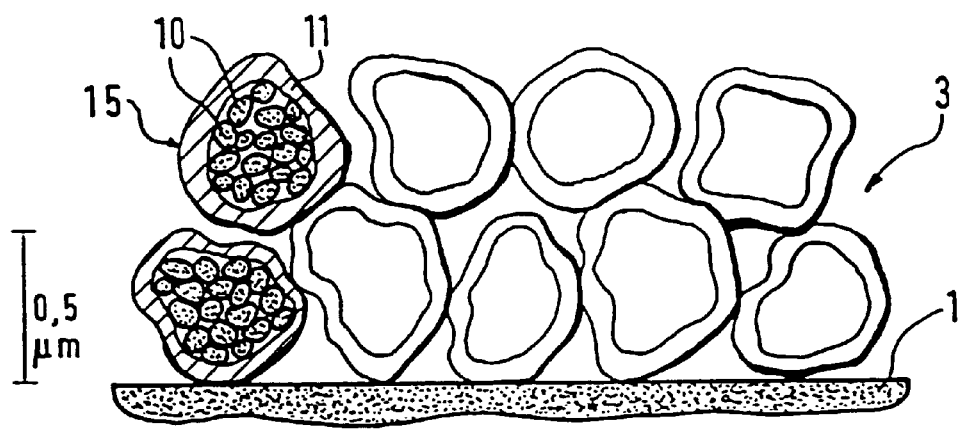
FIG. 6 is an enlarged section of the sensitive semiconductor layer prior to the sintering.

FIG. 1 shows a view from above of a sensor with a rod-shaped design. The basis for this sensor is a substrate 1, composed of an electrically insulating and heat-resistant material, preferably aluminum oxide ($Al_2O_3$), onto which the additional components that form the sensor are deposited in the thick/or thin layer technique. Two conductor tracks 2 with comb-type interlacing of their head ends are initially deposited on a surface of substrate 1, which is referred to in the following as the upper side.

In the region of the interlaced ends, a sensitive, semiconducting metal oxide layer 3 is deposited according to FIG. 2 over the conductor tracks 2 with a layer thickness of 5 to 500 $\mu$m, preferably 20 to 50 $\mu$m. The metal oxide suitably is a stannic oxide ($SnO_2$). However, alternatively it is also possible to use indium oxide ($In_2O_3$), titanium oxide ($TiO_2$) or another n-semiconducting metal oxide or metal mix oxide, to which a conductivity-enhancing doping element has been added in concentrations of 0.001 to 0.5 mol %, preferably 0.005 to 0.015 mol %. If stannic oxide ($SnO_2$), tantalum ($Ta_2O_3$), niobium oxide ($Nb_2O_3$) or mixtures thereof are used, then antimony or tungsten oxides are used as doping elements, while stannic, titanium or Cer-oxides are added if indium oxide ($In_2O_3$) is used. The metal oxide layer 3 is furthermore doped homogeneously with a precious metal additive. It consists preferably of palladium (Pd) in a concentration of 0.5 to 3 mol %, in particular 1.2 mol %, which limits the subsequently deposited gold coating from diffusing into the metal oxide. The precious metal admixture can additionally contain percentages of platinum (Pt) and/or rhodium (Rh) in a concentration of 0.001 to 0.3 mol %, which influence the response speed of the sensor. The metal oxide of layer 3 can also contain admixtures for limiting the crystallite growth following the conclusion of the production process, in particular to prevent the further sintering together of the semiconductor oxide that initially is present in the form of grains, and can thus improve the resistance to aging of the sensors. Suitable admixtures are the oxides of bivalent elements, e.g. magnesium (Mg), barium (Ba), calcium (Ca), strontium (Sr), zinc (Zn) or a trivalent element such as aluminum as oxide ($Al_2O_3$) in concentrations of 0.01 to 0.3 mol %.

Figure 7:
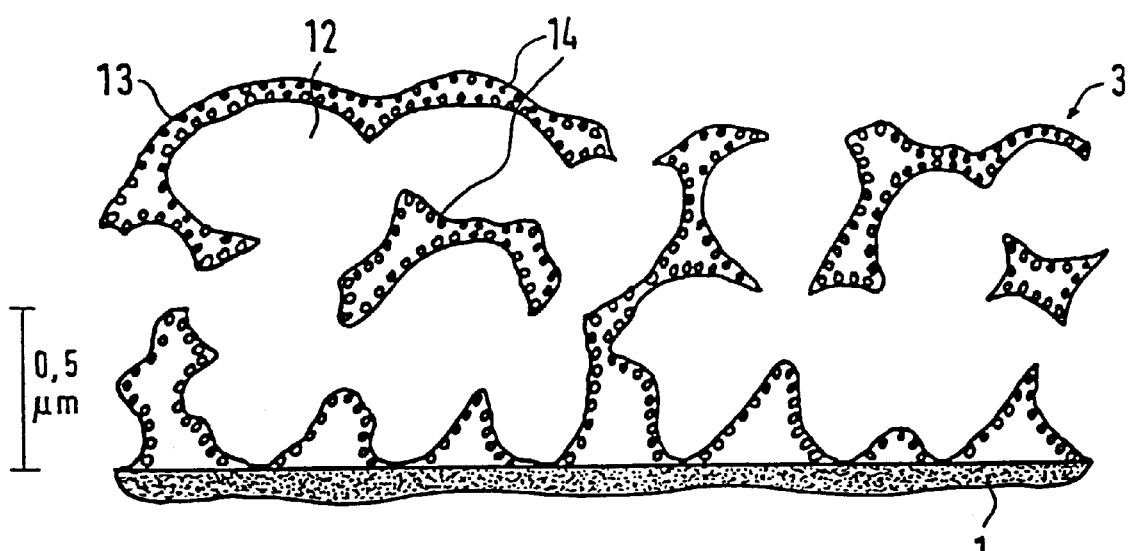
FIG. 7 shows a section of the sensitive semiconductor layer after the sintering.

A further component of the metal oxide layer 3 is gold (Au) in a concentration of 0.3 to 3 mol %, preferably 0.6 mol %, or an alloy of gold and one or several precious metals from the group palladium (Pd), platinum (Pt), rhodium (Rh), iridium (IR), osmium (OS) or silver. As shown in FIG. 7, the gold or gold alloy is not mixed homogeneously with the other components of the metal oxide layer 3, but is deposited such that it forms a surface coating 14 for the structural compounds or composite 12, which are composed of the doped metal oxide. The latter develop during the production by sintering together a basic material that initially is present in the form of grains 15, as shown in FIG. 6. The sponge-like structure of the sensitive layer 3 as shown in FIG. 7, which is composed of the metal oxide with a surface coating of a gold alloy, is responsible for the desired transverse sensitivity of the sensor relative to nitric-oxides. It forms an essential characteristic of the inventive sensor.

As can be seen in FIGS. 3 to 5, a porous protective layer 4 can be deposited over the metal oxide layer 3, advisably with a thickness of approximately 10 to 100 $\mu$m. This layer preferably is composed of aluminum oxide ($Al_2O_3$), titanium oxide ($TiO_2$), zirconium oxide ($ZrO_2$) or silicon dioxide ($SiO_2$). A heating arrangement 5 is located on the opposite side of substrate 1, meaning on the underside, which is shown in FIG. 5 in a view from above. It consists of a meandering conductor track in a region below the sensitive region of the sensor.

A process for manufacturing a metal oxide layer with a sponge-like structure corresponding to FIG. 7 is described in the following. All quantities given are applied to a composition of one mol stannic oxide.

In an introductory processing step, one mol stannic tetrachloride ($SnCl_4$), together with 0.02 mol % tantalum V-chloride ($TaCl_5$) are added to 500 ml hydrochloric acid (HCl). The mixture is dissolved in 30 l water. Stannic oxide ($SnO_2$) is then precipitated out from this watery mixture by adding ammonia ($NH_3$). The precipitated out product is subsequently washed several times, advisably at least three times, through sedimentation. The resulting sediment is then dissolved in 300 ml water by adding 1.2 mol % palladium nitrate and 0.1 mol % magnesium nitrate and is subsequently dried. The product that exists following the drying is calcined for five hours at a temperature of preferably 500° C. and is then ground. It is useful if the resulting grain size is in a range of 1 $\mu$m.

The grinding delivers a powder composed of stannic oxide ($SnO_2$) with shares of 0.01 mol % tantalum oxide ($Ta_2O_5$), 1.2 mol % palladium (Pd), as well as 0.1 mol % magnesium oxide (MgO). The tantalum oxide ($Ta_2O_5$) in this case serves to increase the conductivity, the palladium (Pd) functions as diffusion blocking agent for the subsequent surface coating of the powder grains, while the magnesium oxide (MgO) functions to control the degree of sintering, in particular it prevents a strong sintering together of the grains during the production process. The powder grains have a crystallite microstructure with a crystallite size of approximately 20 to 80 nm.

Following that, a coating is deposited over the powder. In a first step, 0.4 mol % gold (Au) in the form of gold acid ($HAuCL_4$) dissolved in water is deposited over the powder, resulting in a slurry. This slurry is dried. All the gold acid existing in the slurry is subsequently reduced to gold through thermal treatment in a rotary furnace in a water jet with 10% $H_2$ in $N_2$, preferably at approximately 200° C. In a second step, a palladium coating follows this coating with gold. For this, 0.2 mol % palladium (Pd) in the form of palladium nitrate dissolved in water is deposited on the powder previously coated with gold. Again a slurry develops, which is then dried. The dried slurry is treated thermally at a temperature of preferably approximately 200° C. in a rotary furnace and in an air flow. The palladium (Pd) present in the slurry is thereby converted to palladium oxide (PdO) and palladium-coated grains develop.

It is useful if a screen printing paste is produced from the coated powder with the aid of butyl carbitol and ethylcellulose. For the production of a sensor, this paste is applied as sensitive layer 3 over the substrate 1. FIG. 6 illustrates the structure of such a sensitive layer 3 that is applied to a substrate 1. It is composed of adjoining grains 15, the surfaces of which are enclosed in a layer 11. The grains 15 themselves are composed of individual crystallites 10.

The sensors imprinted with the sensitive layer 3 are advisably sintered at 700° C. for about three hours. During this process, the palladium oxide (PdO) present in the layers 11 that envelope the grains 15 changes to palladium (Pd) and alloys with the gold that also exists in the enveloping layers 11. The stannic oxide grains 15 that are initially separate combine to form structural compounds 12 during the sintering, and the enveloping layers 11 that initially surround the individual grains 15 grow together to form a metal coating 14 in the form of small clusters covering the surfaces of the structural compounds 12. FIG. 7 shows the structure of a sensitive layer 3 following the sintering.

It was found that for an operating temperature of approximately 300° C., sensors with a sensitive layer composed of a material produced according to the inventive process when admitted with 40 vpm carbon monoxide (CO) have in air with a relative humidity of 60% as referred to 20° an electrical resistance reduced by a factor of 3 to 5 relative to the value in pure air. When admitting a test gas additionally with 1 to 5 vpm nitric-oxide ($NO_2$), this results in an increase in the electrical resistance of less than 30% for 40 vpm carbon monoxide (CO) and 1–5 vpm nitric-oxide ($NO_2$).

We claim:

1. Sensor for detecting combustible gases in a test gas which sensor displays accuracy and sensitivity even in the presence of nitric oxides, with a sensitive layer on the basis of a semiconducting metal oxide that is deposited on an insulating, ceramic substrate, and for which the electrical resistance delivers a statement on the concentration of combustible gases in a test gas and wherein the sensitive layer (3) has a structural composition (12) of sintered together grains (15) of the semiconducting metal oxide and the surface of sintered together grains in this composition (12) is coated with gold and/or a gold alloy to prevent adsortion of any nitric oxides onto said surface from said test gas.

2. Sensor according to claim 1, wherein the gold alloy is composed of 66 mol % gold and 33 mol % palladium (Pd).

3. Sensor according to claim 1, wherein the gold alloy is composed of gold and one or several precious metals from the group palladium (Pd), platinum (Pt), rhodium (Rh), iridium (IR), osmium (Os) or silver (Ag).

4. Sensor according to claim 1, wherein the alloy is composed of gold with a component of another metal with higher melting point.

5. Sensor according to claim 1, wherein the component of the gold and/or the gold alloy relative to the semiconducting metal oxide is 0.3 to 3 mol %.

6. Sensor according to claim 1, wherein the semiconducting metal oxide has a homogeneous doping with palladium of 0 up to 3 mol %.

7. Sensor according to claim 1, wherein the semiconducting metal oxide is stannic oxide ($SnO_2$).

8. Sensor according to claim 1, wherein the semiconducting metal oxide is indium oxide ($In_2O_3$), titanium oxide ($TiO_2$) or another n-semiconducting metal oxide or metal mix oxide.

9. Sensor according to claim 1, wherein the semiconducting metal oxide is doped with tantalum oxide ($Ta_2O_5$) or niobium oxide ($Nb_2O_5$) at a concentration of 0.001 to 0.05 mol % relative to the semiconducting metal oxide.

10. Sensor according to claim 1, wherein the semiconducting metal oxide is mixed with a 2-valent or 3-valent element of the alkaline earth or the rare earths, at a concentration of 0.03 to 0.3 mol % and preferably 0.1 mol %.

11. Sensor according to claim 1, wherein the sensitive layer has a sponge-like structure.

12. Sensor according to claim 5, wherein the component of the gold and/or the gold alloy relative to the semiconducting metal oxide is approximately 0.6 mol %.

13. Sensor according to claim 6, wherein the semiconducting metal oxide has a homogeneous doping with palladium of 1.2 mol %.

14. Sensor according to claim 9, wherein the semiconducting metal oxide is doped with tantalum oxide ($Ta_2O_5$) or niobium oxide ($Nb_2O_5$) at a concentration of 0.005 to 0.015 mol % relative to the semiconducting metal oxide.

15. Process for producing a sensitive layer for gas sensors, which determine the combustible gas component in a test gas by evaluating the electrical resistance of the sensitive layer, comprising the following steps:

producing a powder (15) on the basis of a semiconducting metal oxide with components of an oxide that increases the conductivity, of palladium as well as of a 2- or 3-valent element of the alkaline earth or the rare earths;

coating the powder grains (15) with gold or an alloy of gold and one or several precious metals of the group palladium (Pd), platinum (Pt), rhodium (Rh), iridium (Ir), osmium (Os);

producing a paste from the coated powder grains;

applying the paste to the sensor substrate (1) as the sensitive layer (3); and sintering the sensitive layer (3) on the substrate (1) at 500° to 1000° C.

16. Process according to claim 15, wherein the production of the powder involves the following steps:

mixing stannic tetrachloride ($SnCl_4$) and tantalum pentachloride ($TaCl_5$) into hydrochloric acid (HCl), dissolving the mixture in water, precipitating out stannic oxide ($SnO_2$) from the solution, sedimentation of precipitated product, dissolving sediments in water, drying solution, calcining dried product, and grinding the calcined product.

17. Process according to claim 15, wherein the powder grains are coated initially with gold and subsequently with palladium.

18. Process according to claim 15, wherein the coating of the powder grains (15) with gold (Au) involves the following steps:

producing a slurry by adding auric acid dissolved in water to the powder, drying the slurry, and thermally treating the slurry in a water flow.

19. Process according to claim 15, wherein the coating of the powder grains (15) with palladium (Pd) involves the following steps:

producing a slurry by adding palladium nitrate ($Pd(NO_3)_2$) dissolved in water to the gold-coated powder (15);

drying the slurry; and thermally treating the slurry in the air flow.

20. Process according to claim 15, wherein the semiconducting metal oxide is stannic oxide ($SnO_2$).

21. Process according to claim 15, wherein the oxide that increases conductivity is tantalum oxide ($Ta_2O_5$).

22. Process according to claim 15, wherein magnesium oxide (MgO) is used as alkaline earth element.

23. Process according to claim 15, wherein the sintering of the sensitive layer takes place at approximately 700° C.

* * * * *